United States Patent [19]

Kornfeld et al.

[11] 4,075,213

[45] Feb. 21, 1978

[54] 8-ARYL-9-ERGOLENES

[75] Inventors: Edmund C. Kornfeld; Nicholas J. Bach, both of Indianapolis, Ind.

[73] Assignee: Eli Lilly and Company, Indianapolis, Ind.

[21] Appl. No.: 773,627

[22] Filed: Mar. 2, 1977

[51] Int. Cl.$^2$ .................. C07D 457/02; A61K 31/48
[52] U.S. Cl. .................................. 260/285.5; 424/261
[58] Field of Search ...................................... 260/285.5

[56] References Cited

U.S. PATENT DOCUMENTS 2,861,074   11/1958   Kornfeld et al. ................ 260/285.5

FOREIGN PATENT DOCUMENTS 786,939   11/1957   United Kingdom ............. 260/285.5

OTHER PUBLICATIONS

Kline et al., J. Org. Chem. vol. 25, pp. 142–143, (1960).

Primary Examiner—Donald G. Daus
Assistant Examiner—Mary Vaughn
Attorney, Agent, or Firm—James L. Rowe; Everet F. Smith

[57] ABSTRACT

8-Aryl-9-ergolenes, α-blockers, serotonin inhibitors, prolactin inhibitors.

11 Claims, No Drawings

8-ARYL-9-ERGOLENES

BACKGROUND OF THE INVENTION

Compounds based on the ergoline ring system:

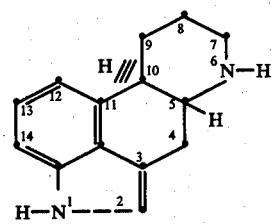

have a suprising variety of pharmaceutical activities. For example, lysergic and isolysergic acid are 8-carboxy-6-methyl-9-ergolenes. (The trivial name "Ergoline" is given to the above structure and the 9,10 double bonded compound-related to lysergic acid-is called a 9-ergolene rather than a 9,10-didehydroergoline). The amides of lysergic acid, many of which have valuable and unique pharmacologic properties, include the naturally occurring oxytocic alkaloids — ergocornine, ergokryptine, ergonovine, ergocristine, ergosine, ergotamine, etc. — and synthetic oxytocics such as methergine as well as the synthetic hallucinogen — lysergic acid diethylamide or LSD. The amides of 6-methyl-8-carboxyergoline, known generically as dihydroergot alkaloids, are oxytoxic agents of lower potency and also lower toxicity than the ergot alkaloids themselves. Recently, it has been found by Clemens, Semonsky, Meites, and their various co-workers that many ergot-related drugs have activity as prolactin inhibitors including ergocornine, dihydroergocornine, 2-bromo-α-ergokryptine and d-6-methyl-8-cyanomethylergoline. References embodying some of the newer findings in the field of ergoline chemistry are the following: Nagasawa and Meites, *Proc. Soc. Exp't'l. Biol. Med*, 135 469 (1970); Lutterbeck et al., *Brit. Med. J.*, 228, (July 24, 1971); Heuson et al., *Europ J. Cancer*, 353 (1970); *Coll. Czech, Chem. Commun.*, 33, 577 (1968); *Nature*, 221, 666 (1969); Seda et al., *J. Reprod. Fert.*, 24 263 (1971); Mantle and Finn, id, 441; Semonsky and co-workers, *Coll. Czech. Chem. Comm.*, 36, 2200 (1971); Schaar and Clemens, *Endocr.*, 90, 285-8 (1972); Clemens and Schaar, *Proc. Soc. Exp, Biol Med.*, 139, 659-662 (1972); Bach and Kornfeld, *Tetrahedron Letters*, 3225 (1974) and Sweeney, Clemens, Kornfeld and Poore, 64th Annual Meeting, American Association Cancer Research, April 1973. Recently issued patents in the field of ergoline derivatives or lysergic acid derivatives include the following: U.S. Pat. Nos. 3,704,233, 3,709,891, 3,585,201, 3,666,762, 3,586,683, 3,717,640, 3,592,816, 3,732,231, 3,717,640, 4,001,242, etc. — see also Patent Office Classification Files 260-256.4 and 260-285.5.

8-Arylergolines have not heretofore been described. However, 2,3-dihydro-6-methyl-8-hydroxy-8-phenyl-9-ergolene is disclosed in U.S. Pat. No. 2,861,074 and in *J. Org. Chem.*, 25, 142 (1960).

SUMMARY OF THE INVENTION

This invention provides 8-aryl-9-ergolenes of the formula:

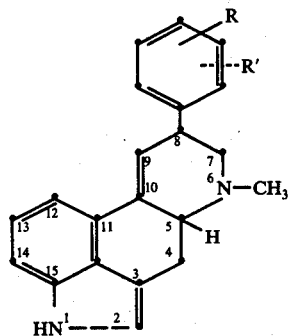

wherein R and R', when taken individually are hydrogen or ortho or para Cl, $C_1$-$C_2$ alkyl, or $C_1$-$C_2$ alkoxy and when taken together on adjacent carbons of the phenyl ring, are methylene dioxy; and pharmaceutically-acceptable acid addition salts thereof formed with non-toxic acids. The term $C_1$-$C_2$ alkyl includes methyl and ethyl and the term $C_1$-$C_2$ alkoxy includes methoxy and ethoxy.

The pharmaceutically-acceptable acid addition salts of this invention include salts derived from inorganic acids such as: hydrochloric acid, nitric acid, phosphoric acid, sulfuric acid, hydrobromic acid, hydriodic acid, nitrous acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Illustrative compounds coming within the scope of this invention include:
 8α-phenyl-6-methyl-9-ergolene maleate,
 8β-phenyl-6-methyl-9-ergolene succinate
 8α-p-tolyl-6-methyl-9-ergolene sulfate
 8α-m-tolyl-6-methyl-9-ergolene mandelate
 8β-o-tolyl-6-methyl-9-ergolene mesylate
 8β-p-ethylphenyl-6-methyl-9-ergolene maleate
 8α-o-ethylphenyl-6-methyl-9-ergolene phosphate
 8α-o-anisyl-6-methyl-9-ergolene hydrobromide
 8α-p-anisyl-6-methyl-9-ergolene lactate
 8β-o-anisyl-6-methyl-9-ergolene benzenesulfonate
 8β-p-ethoxyphenyl-6-methyl-9-ergolene p-toluenesulfonate
 8α-o-ethoxyphenyl-6-methyl-9-ergolene citrate
 8α-3,4-methylenedioxyphenyl-6-methyl-9-ergolene maleate
 8β-2,3-methylenedioxyphenyl-6-methyl-9-ergolene acetate 8α-p-chlorophenyl-6-methyl-9-ergolene 1,4-butyndioate and 8α-o-chlorophenyl-6-methyl-9-ergolene bisulfate The compounds of this invention or their salts are white-crystalline solids and are prepared according to the following general procedure: the tetracyclic allylic alcohol 2,3-dihydro-6-methyl-8-hydroxy-9-ergolene available by the procedure of Kornfeld, et. al., *J. Amer. Chem. Soc.*, 78, 3087 (1956) is reacted with an aromatic substrate of the formula

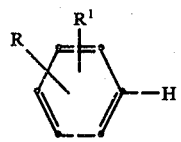

wherein R and R¹ have the same meaning as hereinabove, in the presence of borontrifluoride etherate as a catalyst and in trifluoroacetic acid as a solvent to yield a mixture of 8α and 8β-aryl-2,3-dihydro-6-methyl-9-ergolenes. The components of this mixture are separated by chromatography, the 8α isomer generally being the faster moving isomer. Dehydrogenation of the separated isomers with MnO₂ yields the 8α and 8β-aryl-9-ergolenes of this invention.

The reaction of the tetracyclic allylic alcohol and toluene, anisole, ethoxybenzene, chlorobenzene or ethylbenzene yields predominantly the para isomer, although small amounts of the orthoisomer are detected. Similarly, with 1,2-methylenedioxy-benzene, the 3,4-methylenedioxyphenyl isomer predominates.

This invention is further illustrated by the following specific examples.

EXAMPLE 1

PREPARATION OF 8α and 8β-PHENYL-6-METHYL-2,3-DIHYDRO-9-ERGOLENE

A mixture containing 1.13 g. of 2,3-dihydro-6-methyl-8-hydroxy-9-ergolene, 10 ml. of benzene, 25 ml. of trifluoroacetic acid and 2 ml. of borontrifluoride etherate were stirred for ½ hour at ambient temperature. The reaction mixture was then warmed on a steam bath for 2 hours. The course of the reaction was followed by thin-layer chromatography. The reaction mixture was then poured over ice and made basic to litmus by the addition of dilute aqueous ammonium hydroxide. The aqueous layer was extracted with chloroform. The organic layer was separated, washed with saturated sodium chloride, and dried. Chromatography of the residue over 30 g. of silica gel using chloroform containing 1 percent methanol as the eluant yielded 3 components. The fastest moving (first to elute) component was 8α-phenyl-2,3-dihydro-6-methyl-9-ergolene. Recrystallization of fractions containing this isomer from methanol yielded purified material melting at 152°–153° C. with decomposition. Yield = 34%. The second fraction to elute was 2 spot material by TLC. The third fraction was a one major spot by TLC and was purified by recrystallization from a methanol-ether solvent mixture. 8β-Phenyl-2,3-dihydro-6-methyl-9-ergolene thus purified melted at 211°–213° C. with decomposition. Yield = 31%.

8α-phenyl-2,3-dihydro-6-methyl-9-ergolene had the following analysis:

Calcd.: C, 83.40; H, 7.33; N, 9.26; Found: C, 83.52; H, 7.26; N, 9.05.

Other compounds preparable by the above procedure include: 8α-p-tolyl-6-methyl-2,3-dihydro-9-ergolene melting at 133°–135° C.; after recrystallization from methanol. Yield = 16 percent.

Analysis Calcd.: C, 83.50; H, 7.64; N, 8.85; Found: C, 83.28; H, 7.46; N, 8.59;

8β-p-tolyl-2,3-dihydro-6-methyl-9-ergolene which melted at 144°–146° C. with decomposition after recrystallization from ether; yield = 30 percent.

Analysis Calcd.: C, 83.50; H, 7.64; N, 8.85; Found: C, 83.65; H, 7.78; N, 8.60

8α-p-anisyl-6-methyl-9-ergolene melting at 193°–197° C. with decomposition after recrystallization from methanol; yield = 5 percent.

8β-p-anisyl-6-methyl-2,3-dihydro-9-ergolene melting at 195°–197° C. with decomposition after recrystallization from methanol; yield = 63 percent.

Analysis Calcd.: C, 79.48; H, 7.28; N, 8.43; Found: C, 79.19; H, 7.40; N, 8.27;

8α-3,4-methylenedioxyphenyl-2,3-dihydro-6-methyl-9-ergolene melting at 163°–165° C. with decomposition after recrystallization from methanol; yield = 4 percent.

8β-3,4-methylenedioxyphenyl-2,3-dihydro-6-methyl-9-ergolene melting at 157°–158° C. with decomposition after recrystallization from ethyl acetate. Yield = 46 percent.

Analysis Calcd.: C, 76.28; H, 6.40; N, 8.09; Found: C, 76.07; H, 6.69; N, 8.10;

8-p-chlorophenyl-2,3-dihydro-6-methyl-9-ergolene, an amorphous product; 2 percent yield.

Analysis Calcd.: C, 74.88; H, 6.28; N, 8.32; Found: C, 74.68; H, 6.44; N, 8.19

EXAMPLE 2

PREPARATION OF 8β-p-TOLYL-6-METHYL-9-ERGOLENE

A solution was prepared from 500 mg. of 8β-p-tolyl-2,3-dihydro-6-methyl-9-ergolene in 100 ml. of chloroform. 3 g. of manganese dioxide previously activated were added and the reaction mixture stirred at ambient temperature for ¾ hour. Thin-layer chromatography indicated that the reaction had proceeded substantially toward completion. The reaction mixture was filtered and the filter cake washed with chloroform. The combined filtrate and washings were evaporated to dryness in vacuo. The resulting residue was dissolved in chloroform and the chloroform solution chromatographed over 30 g. of silica gel using chloroform containing 2 percent methanol as the eluant. TLC indicated a major spot, and fractions containing this material, after elution from the column, were combined. The residue resulting from the evaporation of the solvent was recrystallized from ether. 8β-o-Tolyl-6-methyl-9-ergolene thus prepared melted at 228°–30° C. with decomposition; yield = 39 percent.

Analysis Calcd.: C, 84.04; H, 7.05; N, 8.91; Found: C, 83.79; H, 7.26; N, 8.68

Other compounds prepared by the above procedure include: 8α-phenyl-6-methyl-9-ergolene melting at 143°–144° C. after recrystallization from methanol; yield = 53 percent. The compound was converted to the maleate salt which melted at 184°–186° C. after recrystallization from a methanol-ether solvent mixture.

Analysis Calcd.: C, 72.10; H, 5.81; N, 6.73; Found: C, 71.85; H, 5.63; N, 6.51

8β-phenyl-6-methyl-9-ergolene which melted above 200° C. with decomposition; yield = 50 percent. The corresponding maleate salt melted at 203°-204° C. with decomposition after recrystallization from a methanol-ether solvent mixture.

Analysis Calcd.: C, 72.10; H, 5.81; N, 6.73; Found: C, 71.86; H, 5.82; N, 6.47

8β-anisyl-6-methyl-9-ergolene melting at 235°-237° C. after recrystallization from ether; yield = 52 percent.

Analysis Calcd.: C, 79.97; H, 6.71; N, 8.48; Found: C, 79.79; H, 6.97; N, 8.71

The compound was converted to the maleate salt which melted at 206°-208° C. after recrystallization from a methanol-ether solvent mixture.

Analysis Calcd.: C, 69.94; H, 5.87; N, 6.27; Found: C, 70.20; H, 5.69; N, 5.99

8β-3,4-methylenedioxyphenyl-6-methyl-9-ergolene which melted at 260° C. with decomposition after recrystallization from a methanol-chloroform solvent mixture; yield = 22 percent. The corresponding maleate salt melted above 190° C. with decomposition after recrystallization from ether.

Analysis Calcd.: C, 67.82; H, 5.25; N, 6.08; Found: C, 68.11; H, 5.22; N, 6.23

EXAMPLE 3

PREPARATION OF SALTS

Salts of the free bases of this invention are prepared by dissolving the free base in ether and adding an equivalent of a suitable non-toxic acid, for example, maleic acid, also in ether. The salt thus formed, as for example the maleate salt, is insoluble in ether and can be isolated by filtration. Alternatively, the amine base can be dissolved in ethanol and an equivalent of the acid, for example, sulfuric acid, added as an ethanolic solution. In this instance, since the salt thus formed is soluble in the reaction mixture, the salt is isolated by evaporation of the solvent in vacuo. Salts which can be formed by the above procedures include, among others, the hydrochloride, hydrobromide, phosphate, hydrogen phosphate, dihydrogen phosphate, acetate, succinate, tartrate, citrate, benzoate, and p-toluene sulfonate salts.

The compounds of this invention are useful as prolactin inhibitors and/or have activity in the central nervous system. The inhibition of prolactin secretion by compounds of this invention is evidenced by the following experiment: Adult male rats of the Spraque-Dawley strain weighing about 200 g. were used. All rats were housed in an air-conditioned room with controlled lighting (lights on 6 a.m. - 8 p.m.) and fed lab chow and water ad libitum.

Each male rat received an intraperitoneal injection of 2.0 mg. of reserpine in aqueous suspension 18 hours before administration of the ergoline derivative. The purpose of the reserpine was to keep prolactin levels uniformly elevated. The ergoline derivatives under test were dissolved in 10 percent ethanol at a concentration of 1 mg/ml, and were injected intraperitoneally at a standard dose of 1 mg. Each compound was administered to a group of 10 rats, and a control group of 10 intact males received an equivalent amount of 10 percent ethanol. One hour after treatment, all rats were killed by decapitation, and 150 μl aliquots of serum were assayed for prolactin.

The difference between the prolactin level of the treated rats and prolactin level of the control rats, divided by the prolactin level of the control rats, gives the percent inhibition of prolactin secretion attributable to the compounds of this invention. Table 1 which follows gives prolactin inhibition percentages for active compounds coming within the scope of Formula I above tested at the 1 mg/rat level. In the table, column 1 gives the name of the compound and column 2, the percent prolactin inhibition.

TABLE 1
PROLACTIN INHIBITION ASSAY

| Name of Compound | % Prolactin Inhibition |
| --- | --- |
| 8α-phenyl-6-methyl-9-ergolene maleate | 88 |
| 8β-phenyl-6-methyl-9-ergolene maleate | 71 |
| 8B-p-anisyl-6-methyl-9-ergolene maleate | 81 |

As prolactin inhibitors, the compounds are useful in the treatment of inappropriate lactation such as undesired post-partum lactation and galactorrhea. In addition, they can be used to treat prolactin-dependent adenocarcinomas and prolactin-secreting pituitary tumors as well as the following disorders: Forbes — Albright syndrome, Chiari — Frommel syndrome, gynecomastia itself and gynecomastia occurring as a result of estrogenic steroid administration for prostatic hypertrophy, fibrocystic disease of the breast (benign nodules), prophylactic treatment of breast cancer, and breast development resulting from the administration of psychotropic drugs, for example, thorazine, or for prostatic hypertrophy itself.

In using the compounds of this invention to inhibit prolactin secretion or for other pharmacologic action, an 8-aryl-6-methyl-9-ergolene according to Formula I above, or a salt thereof with a pharmaceutically-acceptable acid, is suspended in corn oil and the suspension injected parenterally or fed to a female mammal in amounts varying from 0.01 to 10 mg/kg/day of mammalian weight. Oral administration is preferred. If parenteral administration is used, the injection is preferably by the subcutaneous route using an appropriate pharmaceutical formulation. Other modes of parenteral administration such as intraperitoneal, intramuscular, or intravenous routes are equally effective. In particular, with intravenous or intramuscular administration, a soluble pharmaceutically-acceptable salt of an 8-aryl-6-methyl-9-ergolene is employed. For oral administration, a compound according to Formula I either as the free base or in the form of a salt thereof can also be mixed with standard pharmaceutical excipients and loaded into empty telescoping gelatin capsules or pressed into tablets.

Certain compounds of this invention have also exhibited activity in the muricidal rat assay. About half of any given colony of rats are known to kill a mouse placed in the cage with them within 30 seconds. Rats which demonstrate this propensity are selected for use in the muricidal rat assay in which the compound under test is administered to the rat in increasingly greater dosages and a dose effective to inhibit the muricidal impulse is calculated. Table 2, which follows, gives the results of this assay in which 3 of the compounds of this invention have shown activity. In the table, column 1 gives the name of the compound, and column 2, the median effective dose in milligrams/kilograms for inhibiting muricide.

TABLE 2

MURICIDAL RAT ASSAY

| Name of Compound | Median Effective Dose in mg/kg. |
| --- | --- |
| 8β-p-anisyl-6-methyl-9-ergolene maleate | 10 |
| 8β-3,4-methylenedioxyphenyl-6-methyl-9-ergolene maleate | 10 |
| 8β-phenyl-6-methyl-9-ergolene maleate | 5.0 |

The compounds are also active as α-blockers. In the rat aorta strip assay for α-blocking activity, 8α-phenyl-6-methyl-9-ergolene maleate and 8β-p-anisyl-6-methyl-9-ergolene maleate were 1/10 as active as phentolamine and 8β-phenyl-6-methyl-9-ergolene maleate and 8β-3,4-methylenedioxyphenyl-6-methyl-9-ergolene maleate were as active as phentolamine.

The compounds of this invention also show activity as serotonin inhibitors in the anti-serotonin assays using a rat-stomach fundus strip in vitro. Table 3 which follows gives the anti-serotonin activity of the compounds of this invention compared to that of methysergide. In Table 3, column 1 gives the name of the compound, and column 2, the percent anti-serotonin activity compared to that of methysergide.

Table 3

Anti-Serotonin Assay

| Name of Compound | Anti-serotonin Effect as a Percent of Methylsergide Effect |
| --- | --- |
| 8α-phenyl-6-methyl-9-ergolene maleate | 10 |
| 8β-phenyl-6-methyl-9-ergolene maleate | 50 |
| 8β-p-anisyl-6-methyl-9-ergolene maleate | 100 |
| 8β-3,4-methylenedioxyphenyl-6-methyl-9-ergolene maleate | 50 |

We claim:

1. A compound of the formula:

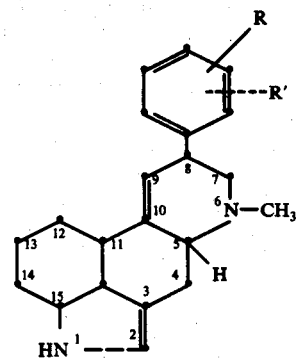

wherein R and R', when taken individually are hydrogen or ortho or para Cl, $C_1$–$C_2$ alkyl, or $C_1$–$C_2$ alkoxy and when taken together on adjacent carbons of the phenyl ring, are methylene dioxy; and pharmaceutically acceptable acid addition salts thereof formed with non-toxic acids.

2. The compound according to claim 1, said compound being 8β-3,4-methylenedioxyphenyl-6-methyl-9-ergolene.

3. The maleate salt of the free base of claim 2.

4. The compound according to claim 1 in which R and R' are both hydrogen.

5. The compound according to claim 3, said compound being 8β-phenyl-6-methyl-9-ergolene.

6. The compound according to claim 4, said compound being 8α-phenyl-6-methyl-9-ergolene.

7. The maleate salt of the free base of claim 5.

8. The maleate salt of the free base of claim 6.

9. The compound according to claim 1, said compound being 8β-p-anisyl-6-methyl-9-ergolene.

10. The maleate salt of the free base of claim 9.

11. The process which comprises the steps of reacting a compound of the formula:

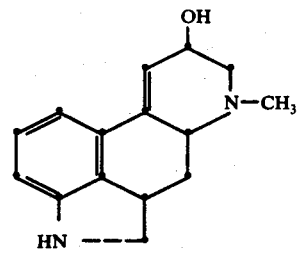

with a compound selected from the group consisting of benzene, toluene, ethylbenzene, anisole, ethoxybenzene, 1,2-methylenedioxybenzene and chlorobenzene, in trifluoroacetic acid in the presence of a catalytic amount of borontrifluoride etherate to yield a compound of the formula:

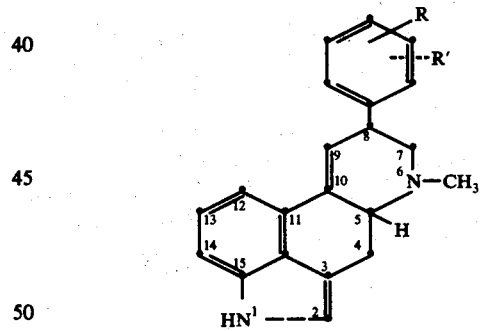

wherein R and R', when taken individually are hydrogen or ortho or para Cl, $C_1$–$C_2$ alkyl, or $C_1$–$C_2$ alkoxy and when taken together on adjacent carbons of the phenyl ring, are methylenedioxy.

* * * * *